(12) United States Patent
Ward et al.

(10) Patent No.: US 7,228,162 B2
(45) Date of Patent: Jun. 5, 2007

(54) ANALYTE SENSOR

(75) Inventors: W. Kenneth Ward, Portland, OR (US);
Richard G. Sass, Portland, OR (US);
Mark Nynest, Gastonia, NC (US);
Ellen Anderson, Tualatin, OR (US);
Lawrence B. Jansen, Portland, OR (US)

(73) Assignee: iSense Corporation, Portland, OR (US)

( * ) Notice: Subject to any disclaimer, the term of this patent is extended or adjusted under 35 U.S.C. 154(b) by 293 days.

(21) Appl. No.: 10/342,144

(22) Filed: Jan. 13, 2003

(65) Prior Publication Data

US 2004/0138541 A1 Jul. 15, 2004

(51) Int. Cl.
*A61B 5/05* (2006.01)
*A61B 5/00* (2006.01)

(52) U.S. Cl. ............. 600/345; 600/347; 600/365; 204/403.01

(58) Field of Classification Search .......... 600/583
See application file for complete search history.

(56) References Cited

U.S. PATENT DOCUMENTS

| | | | | |
|---|---|---|---|---|
| 4,953,552 | A | 9/1990 | DeMarzo | 128/635 |
| 5,448,992 | A * | 9/1995 | Kupershmidt | 600/347 |
| 5,510,266 | A | 4/1996 | Bonner et al. | 436/43 |
| 5,680,858 | A * | 10/1997 | Hansen et al. | 600/345 |
| 5,791,344 | A * | 8/1998 | Schulman et al. | 600/347 |
| 5,820,622 | A * | 10/1998 | Gross et al. | 604/890.1 |
| 5,871,494 | A | 2/1999 | Simons et al. | 606/181 |
| 6,228,100 | B1 * | 5/2001 | Schraga | 606/183 |
| 6,721,586 | B2 * | 4/2004 | Kiser et al. | 600/345 |
| 6,793,632 | B2 * | 9/2004 | Sohrab | 600/573 |
| 6,830,551 | B1 * | 12/2004 | Uchigaki et al. | 600/584 |
| 6,952,604 | B2 * | 10/2005 | DeNuzzio et al. | 600/345 |
| 2003/0223906 | A1 * | 12/2003 | McAllister et al. | 422/58 |

FOREIGN PATENT DOCUMENTS

| | | |
|---|---|---|
| EP | 0964060 A2 | 12/1999 |
| WO | WO 97/42882 A1 | 11/1997 |
| WO | WO 01/64105 A1 | 9/2001 |
| WO | WO 01/73124 A2 | 10/2001 |

* cited by examiner

*Primary Examiner*—Robert L. Nasser
*Assistant Examiner*—Patricia Mallari
(74) *Attorney, Agent, or Firm*—Schwabe Williamson & Wyatt

(57) ABSTRACT

A method of measuring an analyte concentration in body fluid in an animal body having skin and subcutaneous soft tissue that includes body fluid. The method comprises, introducing a portion of an analyte-measuring device into the subcutaneous soft tissue. The analyte-measuring device includes an analyte sensing element, having a sharpened distal end to facilitate introduction into the animal body. Additionally the sensing element has an indicating electrode that is adapted to be activated by electric power and to form a raw analyte measurement, when it is activated and in contact with the body fluid, in less than two minutes. The sensing device further has a reference electrode and an electric power and display device that is adapted to mate to the analyte-sensing element. The power and display device activates the analyte-sensing element by applying electric power to it. The analyte-sensing element is introduced into the animal body and is activated by the electric power and display device, thereby causing the analyte-sensing element to form a raw analyte measurement. The power and display device forms and displays a second analyte measurement that is related to the raw analyte measurement, within two minutes of the analyte sensing element being introduced into the body.

17 Claims, 4 Drawing Sheets

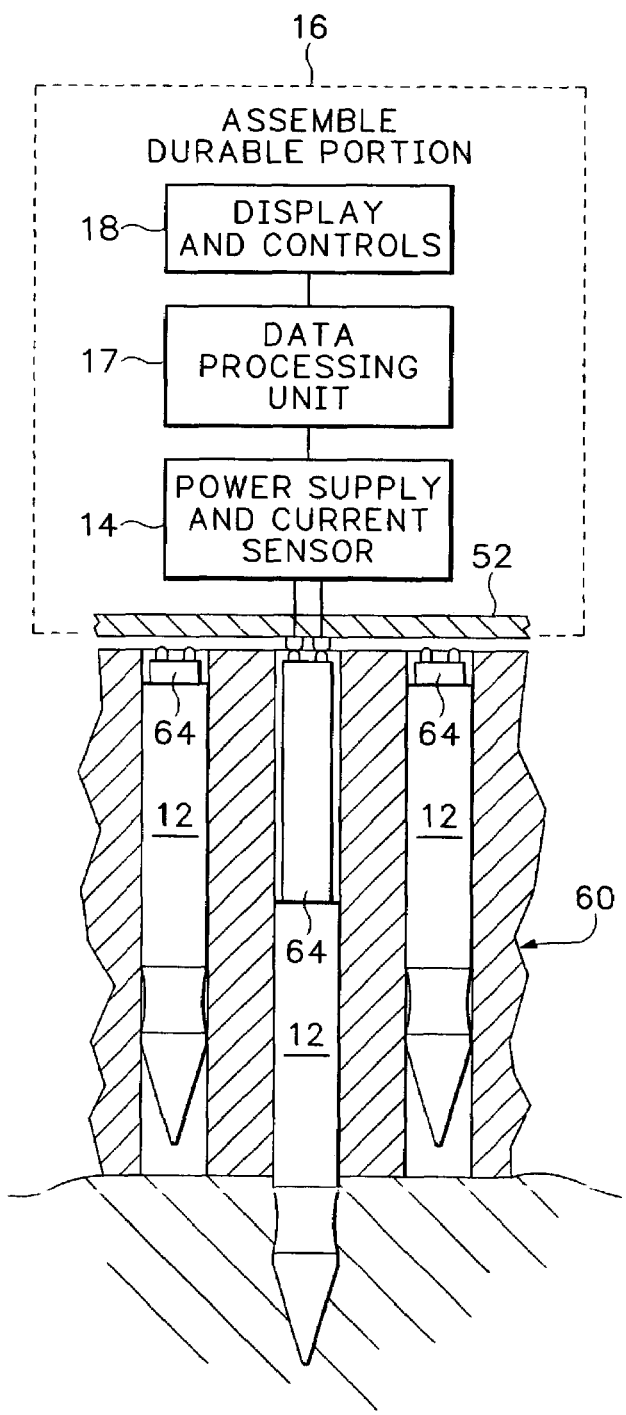
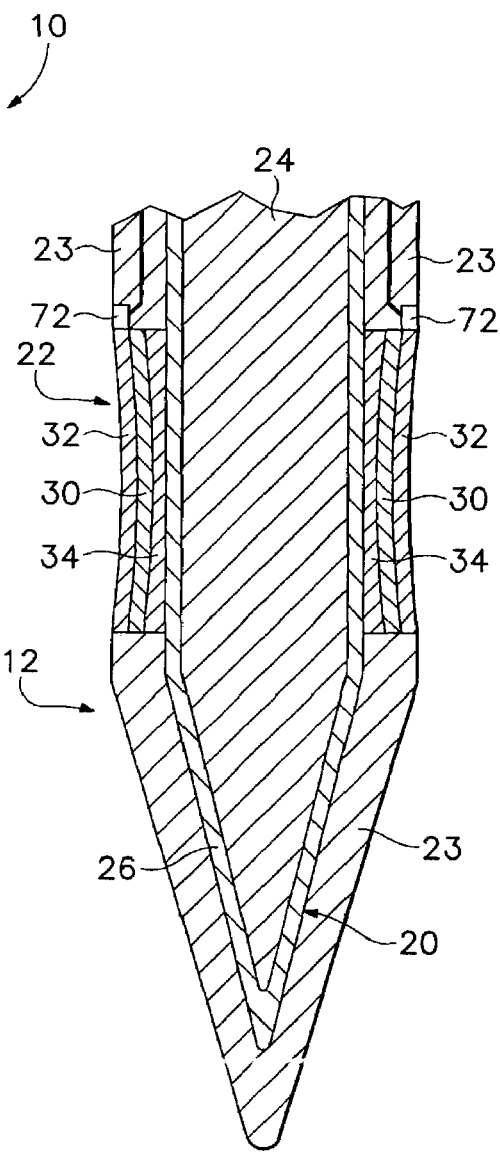
FIG.1
FIG.2

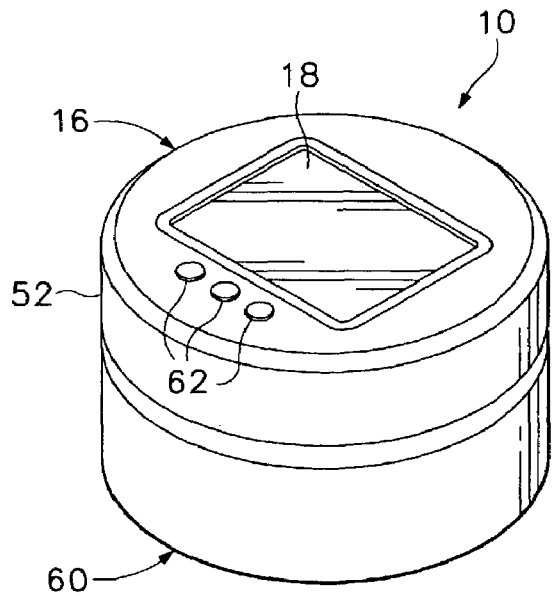
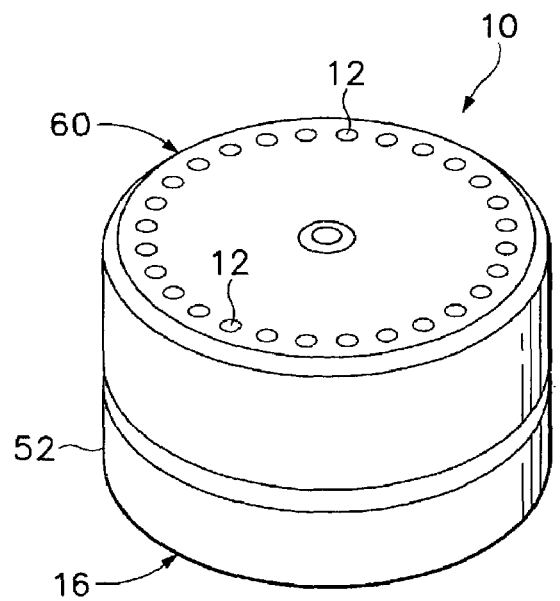
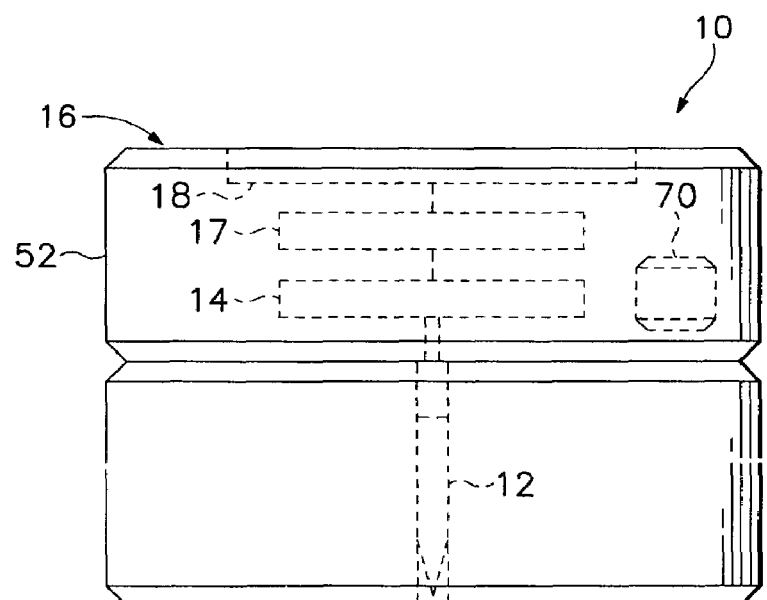

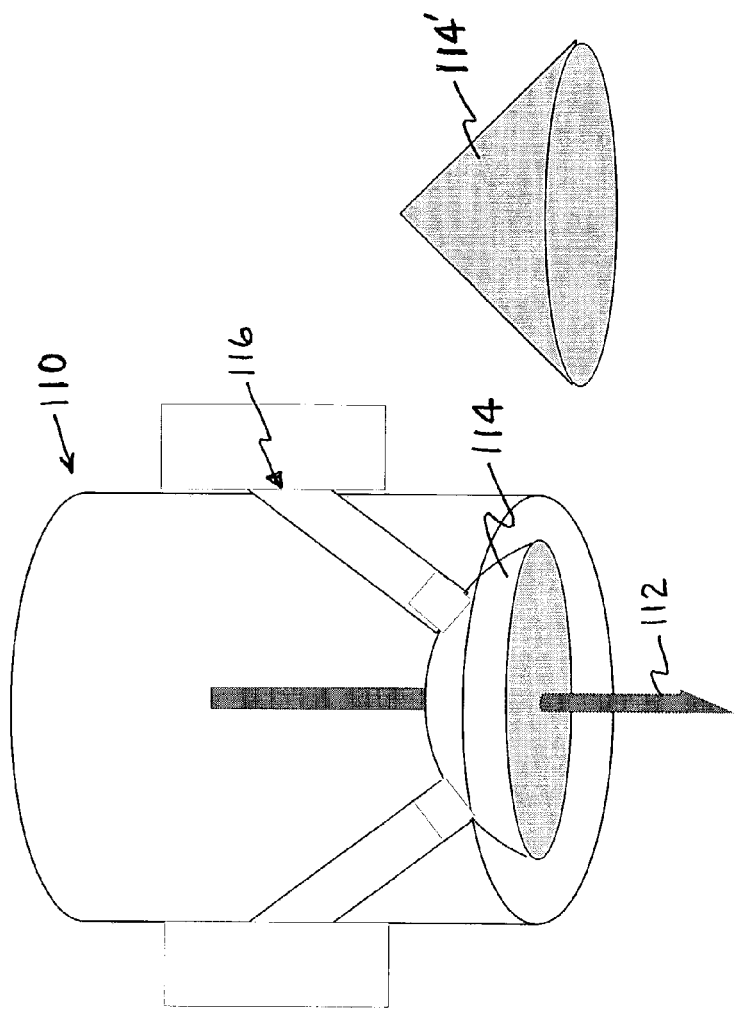
FIG. 7C
FIG. 7B
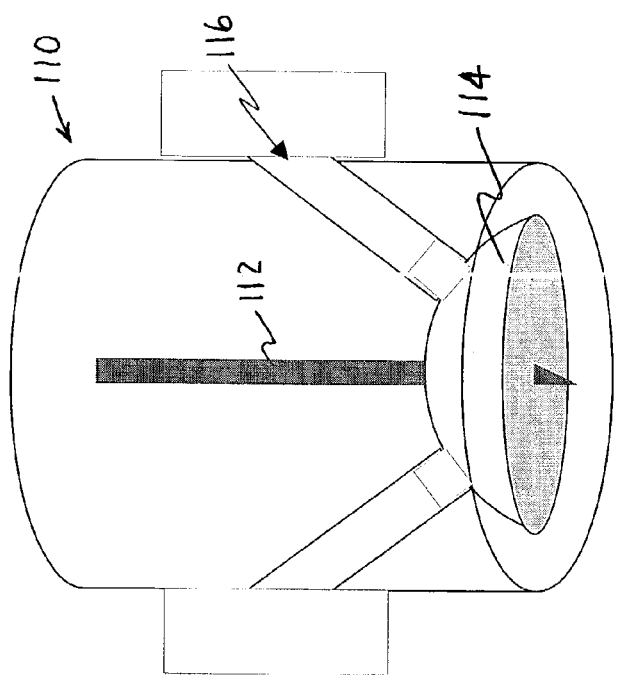
FIG. 7A

ANALYTE SENSOR

BACKGROUND OF THE INVENTION

Among the other unpleasant aspects of having the disorder diabetes mellitus is the need to frequently test one's blood glucose concentration. With current technology a diabetic patient must prick his own fingertip or other body part with a lancet in order to withdraw blood from the wound. The fingertip is preferred because of the great number of capillaries located there.

The broach created through the skin by the lancet must be wide enough to permit blood to flow through. Human epidermis around the fingertips is on the order of 1-3 millimeters thick. Also, similar to other flexible, sheet like materials, skin tends to close up on itself if broached. Accordingly the lancet used must create a broach that is wide enough to not be closed by the natural action of the skin.

Moreover, the task of sampling one's own blood has generally required that a flat surface be present for the patient to arrange various test articles including a test strip, a lancet and a cotton ball with alcohol, for sterilizing the wound. As a result, it has heretofore been impossible for a diabetic patient to measure his blood glucose level in a public place without drawing attention to himself. Interviews with diabetic patients indicate that the workplace, where there is frequently a definite lack of privacy and where maintaining the secrecy of personal information may be greatly desired, presents particular difficulties.

A number of disclosures are aimed at easing this requirement by providing an integrated unit having a number of lancets and associated test articles (such as a test strip or a sensing cavity to be filled with blood drawn out from the body) and in which both lancet and test article are contemporaneously moved into test position. These devices tend to use chemical test strips, rendering them rather bulky and typically requiring the user to place a test strip in place before use.

In addition, a number of disclosures are directed at an implantable or insertable sensor, for continuous glucose monitoring. Although this technology appears to bear promise it is desirable to have additional options for the diabetic patient. For example, a method of quickly and easily making an occasional determination of blood glucose concentration would be helpful for patients not wishing to wear a glucose monitor.

Ease of use is not only an important consideration from the perspective of patient comfort, but also from the perspective of patient health. The easier it is for a patient to take his blood glucose level reading, the more frequently he is likely to do so. In turn, with more frequent measurements, the patient is likely to do a better job at regulating his glucose level and thereby avoiding chronic complications in which body tissue is damaged by toxic glucose levels or acute complications in which the patient is in danger of entering a state of hypoglycemic shock. Moreover, by more frequently measuring his or her glucose levels, the patient will likely form a better understanding of his body's response to the consumption of varying types of food and of varying degrees of physical exertion. The better the patient understands his body's response characteristics the better he will be able to tailor his eating, exercise and insulin injection or ingestion regime.

SUMMARY

In a first separate aspect, the present invention is a method of measuring an analyte concentration in body fluid in an animal body having skin and subcutaneous soft tissue that includes body fluid. The method comprises, introducing a portion of an analyte-measuring device into the subcutaneous soft tissue. The analyte-measuring device includes an analyte sensing element, having a sharpened distal end to facilitate introduction into the animal body. Additionally the sensing element has an indicating electrode that is adapted to be activated by electric power and to form a raw analyte measurement, when it is activated and in contact with the body fluid, in less than two minutes. The sensing device further has a reference electrode and an electric power and display device that is adapted to mate to the analyte-sensing element. The power and display device activates the analyte-sensing element by applying electric power to it. The analyte-sensing element is introduced into the animal body and is activated by the electric power and display device, thereby causing the analyte-sensing element to form a raw analyte measurement. The power and display device forms and displays a second analyte measurement that is related to the raw analyte measurement, within two minutes of the analyte sensing element being introduced into the body.

In a second separate aspect the present invention is an analyte sensing apparatus including a skin-piercing portion that has a thickness of less than 300 micrometers and is adapted to pierce the skin and enter the soft tissue of an animal body.

In a third separate aspect the present invention is an analyte sensing assembly, comprising a housing having at least one opening and a magazine, positioned within the housing and having a plurality of longitudinal storage locations. A substantially longitudinal analyte sensing element is stored in a storage location. Also, an actuator is adapted to controllably move a longitudinal sensing element that is in alignment to an opening, so that it protrudes out of the opening and, afterwards, to move the longitudinal sensing element back so that it is completely enclosed in the housing.

In a fourth separate aspect, the present invention is a method of facilitating the use of an analyte concentration measurement assembly. The assembly has at least one analyte sensing element, which is adapted to accept electric power and to be introduced, at least in part, for less than five minutes into an animal body, and which forms an analyte concentration measurement. Additionally, the assembly has a durable portion matingly connected to and responsive to the analyte sensing element, and adapted to supply the analyte sensing element with electric power, measure the resultant electrical current and display the analyte concentration measurement. The method comprises selling replacement analyte sensing elements, each one adapted to be matingly connected to the electric power and display unit.

In a fifth separate aspect, the present invention is a method of facilitating the use of an analyte concentration measurement assembly. The assembly has at least one magazine, loaded with analyte sensing elements that are adapted to be introduced, at least in part and for less than five minutes into an animal body. The assembly also has an electronic power and display unit, matingly and conductively connected to and responsive to the analyte sensing element and adapted to supply the analyte sensing elements with electric power, measure the resultant current through the indicating electrode and display the analyte concentration measurement. The method comprises selling replacement magazines loaded with analyte sensing units.

In a sixth separate aspect, the present invention is a rapid response analyte sensor assembly, including an active surface of a material that is subject to oxidation, and produces an initial transient current when exposed to oxygen, and that also produces a current when exposed to the analyte. In addition the active surface produces a raw analyte measurement. The sensor assembly includes a current sensing and data analysis unit electrically connected to the active surface. This unit is configured to begin a timing process upon first sensing a current at the active surface and it provides a refined analyte measurement by correcting the raw analyte measurement taken at a first time subsequent to this first sensing of a current by subtracting out a quantity related to the initial transient current expected to exist at that time.

In a seventh separate aspect the present invention is a rapid response, briefly indwelling, analyte sensor assembly, adapted to provide a reading of an analyte concentration within 20 seconds of being introduced into a mammalian body.

In an eighth separate aspect the present invention is a rapid response, single use analyte sensor, adapted to measure an analyte concentration in blood. The sensor includes a lancet and a blood trapping structure, adapted to trap blood on the skin. An electrochemical analyte measurement system measures the analyte concentration in the blood that is trapped on the surface of the skin, by the blood trapping structure.

In a ninth separate aspect, the present invention is a method of measuring the concentration of an analyte in the blood of a patient. The method includes using a rapid response, single use analyte sensor having a lancet, a blood trapping structure for trapping blood on the skin surface and an electrochemical analyte measurement system adapted to measure an analyte concentration in blood that is trapped on the skin surface, by the blood trapping structure. In the method, the skin is punctured with the lancet, permitting blood to flow into the blood trapping structure. The electrochemical analyte measurement system measures the analyte concentration in the blood.

The foregoing and other objectives, features and advantages of the invention will be more readily understood upon consideration of the following detailed description of the invention, taken in conjunction with the accompanying drawings.

BRIEF DESCRIPTION OF THE DRAWINGS

FIG. 1 is a partially schematic representation, partially cross-sectional view of a glucose sensing assembly according to the present invention.

FIG. 2 is an expanded cross-sectional view of a glucose-sensing element of the glucose sensing assembly of FIG. 1.

FIG. 3 is a top perspective of the glucose sensing assembly of FIG. 1.

FIG. 4 is a bottom perspective of the glucose sensing assembly of FIG. 1.

FIG. 5 is a side view of the glucose sensing assembly of FIG. 1.

FIG. 7A is a perspective side view of a single use analyte sensor, in its undeployed state, according to an alternative embodiment of the present invention.

FIG. 7B is a perspective side view of the single use analyte sensor of FIG. 7A, in its deployed state.

FIG. 7C is a perspective view of a variant blood trap, that could be used as part of the embodiment of FIGS. 7A and 7B.

DETAILED DESCRIPTION OF THE PREFERRED EMBODIMENT

Figure 6:
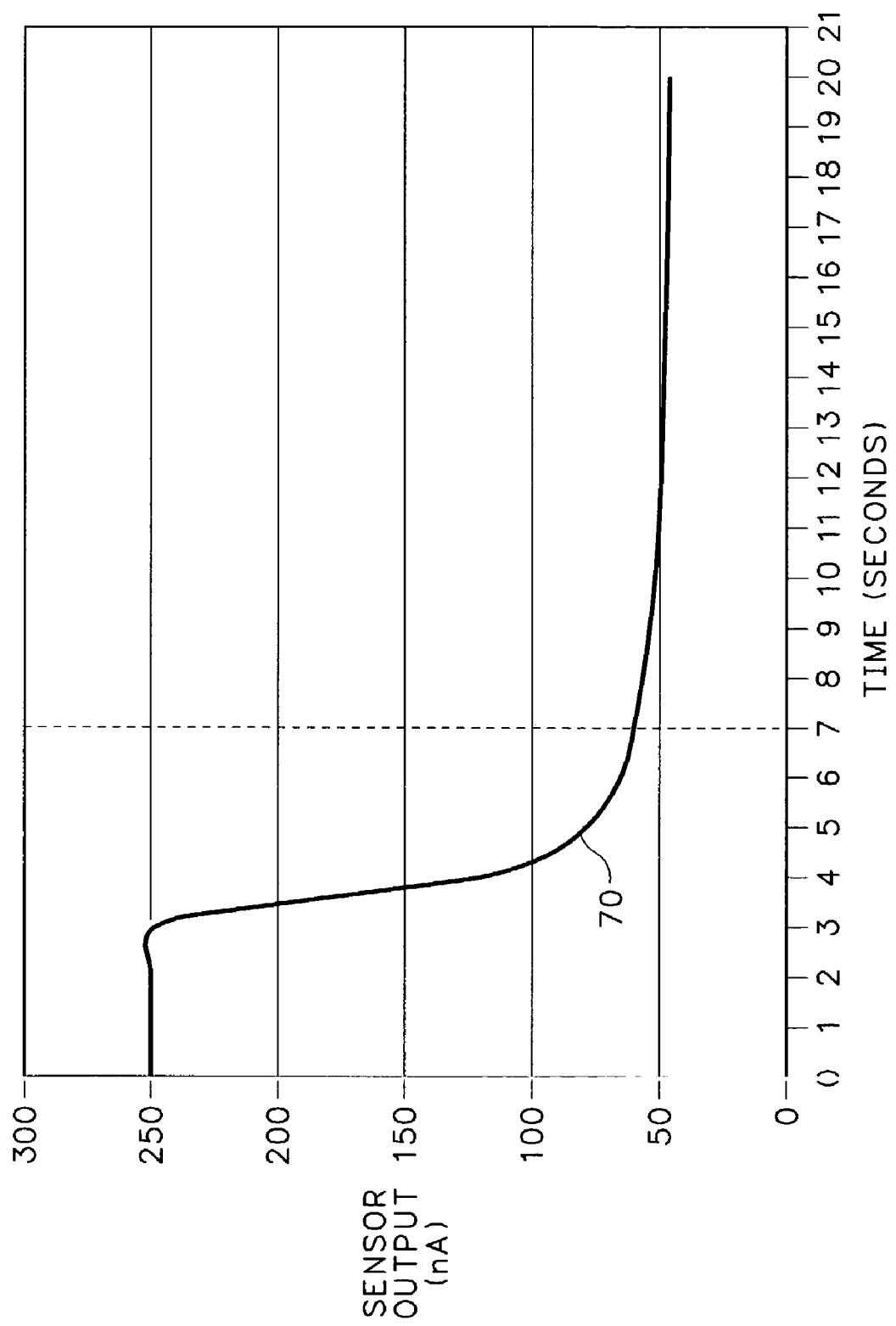
FIG. 6 is a set of graphs showing current versus time for a glucose-sensing element, such as that of FIG. 2, when introduced into any one of three different concentrations of glucose.

Referring to FIG. 1 a preferred embodiment of the present invention is a glucose sensor assembly 10 having a sensing element 12 that is adapted to be briefly introduced into the soft tissue of a patient. A power supply and current sensor unit 14, which is housed in an assembly durable portion 16, supplies the sensing element 12 with power. Sensing unit 14 quickly (<20 seconds) responds to introduction into the soft tissue of a patient by producing a sensing current that is generally proportional to the glucose level in this tissue. This current may be considered a "raw analyte measurement." A data processing unit 17, measures the magnitude of this current, computes a best estimate glucose concentration (or a "refined analyte measurement") and sends this information to a controls and display unit 18, which displays this estimate on a small liquid crystal display. Units 14, 17 and 18 may be collectively termed an "electric power, data processing and display device." It should be noted that although in one preferred embodiment, described above, a fixed voltage is provided and a current is measured, in an alternative preferred embodiment, a fixed current is provided and the voltage across sensing element 14 is measured and is accordingly, the "raw analyte measurement."

Because sensing element 12 yields the sensing current during its brief indwell period, there is no need to withdraw blood from the body. As a result, sensing element 12 is thinner at its distal end (<300 micrometers thick) than lancets adapted to create a puncture through the skin that is sufficient to permit blood flow therethrough.

Referring to FIG. 2, sensing element 12 includes a bimetallic needle 20 that in conjunction with a membrane system 22 reacts to the presence of glucose and oxygen to act as an indicating electrode. Needle 20 is coated with a protective layer 23, made of durable, non-toxic material such as polyimide, except for where coated by membrane system 22. In production, protective layer 23 is dip-coated onto needle 22 and then removed, preferably with an excimer or ND:YAG laser, in the area in which membrane system 22 is to be applied.

Needle 20 has a diameter of 227 microns and has a needle core 24 of structurally robust material such as stainless steel that is 226 microns thick and an electrochemically active plating 26, such as platinum, that is less than a micron thick.

The membrane system 22 must perform a number of functions. First, it must provide an enzyme that reacts with glucose and oxygen to form an electrolyte. A reactive layer 30 of glucose oxidase, glutaraldehyde and albumin produces hydrogen peroxide when contacted by glucose and oxygen, performs this function.

Second, because glucose is far more prevalent in the blood and other body fluids than oxygen, system 22 must include a membrane placed over the reactive layer 30 to permit a greater permeation of oxygen than glucose, so that the glucose concentration measurement is not limited by the oxygen concentration in the immediately surrounding tissue. This function is performed by a permselective hard block/soft block copolymer layer 32. This layer is of the type described in U.S. Pat. Nos. 5,428,123; 5,589,563 and 5,756,632, which are hereby incorporated by reference as if fully set forth herein. Layer 32 is preferably less than 10 microns thick, to permit rapid permeation by glucose and oxygen.

Third, membrane system 22 must prevent interferents, such as acetaminophen, from corrupting the measurement by causing current flow unrelated to the presence of glucose. This function is performed by an inner interferent reducing layer 34 of a compound such as sulfonated polyether sulfone, polyamino-phenol, or polypyrrole, in one embodiment 3-amino-phenol, which quickly permits the permeation of the hydrogen peroxide, which causes the current flow indicative of the concentration of glucose. Persons skilled in the relevant arts will readily recognize that quick permeation is highly desirable in a briefly indwelling sensor so that a measurement may be quickly obtained.

To produce sensing element 12, first the interferent reducing layer 34 of 3-amino-phenol is solution-coated or electro polymerized onto the surface of platinum plating 26. Layer 34 may be from a few nanometers to 2 microns thick, to permit rapid permeation by $H_2O_2$ ions, thereby reacting very quickly to glucose concentration. Over this the reactive layer 30 of glucose oxidase is dip-coated or electrodeposited. Glutaraldehyde is deposited on the glucose oxidase to immobilize the glucose oxidase. The sensor is dip coated in the soft block/hard block copolymer 32. In the finished product, the surface of the sensing region 22 is slightly depressed relative the remainder of the surface of sensing element 12. In one embodiment, the glucose oxidase 30 is applied before layer 34, which is electrodeposited through layer 30.

For sensing assembly 10, in one embodiment, a case 52 of the durable portion 16 serves as a reference electrode. The user grasps the case 52 in his right hand (left hand if the patient is left handed) and pushes a sensing element 12 into either his left arm or a left hand fingertip. When sensing element 12 enters the user's flesh, the circuit is completed through the user's body. Other reference electrode structures can consist of the portion of the housing immediately surrounding the indicating electrode or a patch placed upon the skin.

Referring to FIGS. 3-5, sensing elements 12 are preferably disposable and are provided in a disposable magazine 60, which is releasably and matingly attached to durable portion 16. Magazine 60 is rotated either manually or by pressing one of a set of buttons 62 that are part of the controls and display unit 18. In the second option a small electric motor 70 is actuated that rotates magazine 60. In either embodiment, an unused sensing element is rotated to an activation position, where it is aligned with an opening through the bottom of case 52. When a sensing element 12 is rotated into place, it is automatically electrically connected to the power supply and current sensing unit 14. On command from one of the buttons 62, or in an alternative embodiment always upon arriving sensing element 12 arriving in place, a sensor physical actuation unit 64 pushes sensing element 12 outwardly so that it will enter the flesh of the patient if assembly 10 is correctly positioned against the patient's skin.

In one preferred embodiment the sensing element 12 is energized to a voltage level of 0.65 volts between cathode and anode contemporaneously with being introduced into the patient. In one embodiment a pair of contacts 72 positioned at the top of the sensing region 22 are electrically connected by body fluid when the sensing region 22 is entirely covered by body fluid. This is used to trigger the application of voltage to the sensing element 12.

After insertion the patient waits for approximately six seconds at which time the controls and display unit 18 provides a reading of the blood glucose level. After this, unit 64 pulls sensing element 12 back into magazine 60, where it is stored until all of magazine 60 is detached from the durable portion 16 and placed in a proper disposal receptacle. Subsequently, a new magazine 60 is attached into durable portion 16, for further measurements. To support this option, in a preferred method, new magazines 60, filled with sensors 12 are made and sold. Alternatively, the entire assembly 10 is disposable and comes as a single non-separable unit.

Referring to FIG. 6, which shows a graph 70 of early experimental readings (in current v. time coordinates) from a sensor according to the present invention after being placed in a solution of 5 mM glucose. The current reading at first entry into the solution is heavily corrupted by platinum oxidation and other, incompletely understood, factors. In one preferred embodiment the data processing unit 17, corrects the sensing element current by subtracting away a quantity representing the initial transient current at the moment the sensing element current is measured. To do this, a timing process is started at the moment when sensing element current is first detected. In one embodiment a set of corrected current measurements are averaged together to provide the reading. The correction for the anticipated initial transient current and the use of ultra-thin (for some embodiment less than 10 nanometers thick) membranes permits the calculation of a glucose concentration measurement within 20 seconds of the sensor being introduced into the patient's flesh. As noted, in a preferred embodiment a reading is provided in about 5 seconds. It is possible, in fact likely, that the glucose level will be changing as the unit is in the body.

Accordingly, in one preferred embodiment the direction of change, after correction for the initial transient current, is computed and displayed. In another embodiment a weighted average is formed of the corrected measurements, with more recent measurements being weighted more heavily, to give the patient a reading that reflects more heavily the more recent measurements. In yet another preferred embodiment, the processor simply waits until the initial transient current has dissipated, and then computes an instantaneous or brief period glucose concentration at the latest possible moment, in order to provide the patient with the timeliest information.

In an additional preferred embodiment, the signal processing unit 17 time tags and stores each glucose concentration estimate and uses this stream of time tagged estimates to send a value representing glucose concentration change to the controls and display unit 18.

In order to process the various measurements identified above, including refined glucose concentration estimates, glucose concentration changes, and other refined analyte measurements, during a time in which the sensing element is not indwelling, the computation of such values may be carried out after the analyte sensing element has been removed from the patient. While the raw analyte measurements may be determined fairly quickly, for example within 20 seconds, the refined analyte measurements require one or more additional computations to be performed. Thus, an embodiment of the present invention provides a system in which an analyte sensing element retains body fluid in contact with an indicating electrode after the analyte sensing element is removed from the body, and wherein the analyte sensing element is removed from the body prior to a refined analyte measurement being formed.

Referring to FIGS. 7A-7C, in an additional preferred embodiment of an analyte sensor assembly 110, a lancet 112 is provided to puncture the skin and a blood trap 114 is provided to retain the blood drawn from the broach created by lancet 112. Lancet 112 is somewhat thicker (>300 micrometers thick) than sensing element 12, to ensure that blood is drawn from the wound created. A pair of air vents 116 is provided to permit air to vacate trap 114. In this embodiment lancet 112 is quickly withdrawn, thereby avoiding pain to the patient. In one preferred embodiment lancet 112 is also the indicating electrode and includes a membrane system, such as 22 (FIG. 2), to create an analyte related current, with trap 114 serving as the reference electrode. In an alternative preferred embodiment, trap 114 is the indicating electrode and is coated with a membrane system such as system 22. Trap 114 preferably defines only a small volume and quickly fills with blood after lancet 112 punctures the skin, permitting analysis and answer in only 5 to 10 seconds. Assembly 110, may alternatively include a differently shaped blood trap 114', as shown in FIG. 7C.

The terms and expressions which have been employed in the foregoing specification are used as terms of description and not of limitation, and there is no intention, in the use of such terms and expressions, of excluding equivalents of the features shown and described or portions thereof, it being recognized that the scope of the invention is defined and limited only by the claims which follow.

The invention claimed is:

1. A method of measuring an analyte concentration in body fluid in an animal body having skin and subcutaneous soft tissue that includes body fluid, said method comprising:
    (a) providing an analyte measuring device, including:
        (i) an analyte sensing element having an indicating electrode, said indicating electrode being adapted to be activated by electric power, and to form a raw analyte measurement when so activated and in contact with said body fluid; and
        (ii) an electric power, data processing and display device adapted to mate to said analyte sensing element and activate said analyte sensing element by applying electric power to it and adapted to receive said raw analyte measurement and to compute and display a refined analyte measurement, related to said raw analyte measurement;
    (b) introducing said analyte sensing element into said animal body subcutaneous soft tissue, thereby placing said indicating electrode into contact with said animal body subcutaneous soft tissue and said body fluid;
    (c) activating said analyte sensing element by applying electric power to it, thereby causing said analyte sensing element to form a raw analyte measurement;
    (d) removing said analyte sensing element from said soft tissue after the raw analyte measurement is formed; and
    (e) wherein said analyte sensing element retains body fluid in contact with said indicating electrode after said analyte sensing element is removed from said body, and wherein said analyte sensing element is removed from said body prior to a refined analyte measurement being formed.

2. The method of claim 1, wherein said analyte measuring device further includes a housing and wherein said analyte sensing element is adapted to be withdrawn into said housing and placed therein in a state wherein reuse is impractical.

3. The method of claim 1, wherein said analyte sensing element further includes a sharpened distal and said indicating electrode and said sharpened distal end are physically coincident.

4. The method of claim 1, wherein said analyte sensing element is in the form of a sharpened tube and said indicating electrode is inside said tube.

5. The method of claim 4, wherein at least a portion of said sharpened tube serves as a reference electrode.

6. The method of claim 1, wherein said analyte sensing element includes a reference electrode that is adapted to abut the skin during the formation of an analyte measurement.

7. The method of claim 1, wherein said analyte measuring device includes a housing and wherein said analyte sensing element and said electric power, data processing and display device are operatively connected to said housing.

8. The method of claim 1, wherein said analyte measuring device includes a housing having a housing aperture and at least a first analyte sensing element and a second analyte sensing element and wherein before said analyte measuring device is ever used, both said first analyte sensing element and said second analyte sensing element are stored in an inactive state, enclosed by said housing, but at the time of the first use of said device said first analyte sensing element is deployed into an active state, at least in part protruding through said housing aperture and after said first use said first analyte sensing element is withdrawn into said housing and placed in an inactive storage state and further wherein at the time of the second use of said device said second analyte sensing element is deployed into said active state and after said second use said second analyte sensing element is withdrawn into said housing and stored in said inactive storage state.

9. The method of claim 8, wherein said first analyte sensing element and said second analyte sensing element are held, during said inactive storage state, at a sub unit that is releasably attached to said housing.

10. The method of claim 9, wherein said sub unit is a magazine having at least two sensing element holders, and wherein said sensing elements are held by said magazine both before and after use.

11. The method of claim 1, wherein said electric power, data processing and display device applies electric power to said analyte sensing element by providing a known voltage between said indicating electrode and a reference electrode, and said raw analyte measurement is in the form of an electrical current that is related to glucose concentration and said electric power, data processing and display device receives said raw analyte measurement by measuring said electrical current.

12. The method of claim 1, wherein said electric power, data processing and display device measures said electric current at more than one instance in time and uses a resulting plurality of raw analyte measurements to form a single refined analyte measurement.

13. The method of claim 1, wherein said electric power, data processing and display device forms said refined analyte measurement, in part, by subtracting an initial transient current from said raw analyte measurement, said initial transient current being present when said raw analyte measurement begins in vivo.

14. The method of claim 1, wherein said refined analyte measurement includes an indication of a direction of change in analyte concentration.

15. A method, comprising:
    introducing an analyte sensing element into an animal body;
    applying electric power to said analyte sensing element to form a raw analyte measurement;
    removing said analyte sensing element from said animal body, after the raw analyte measurement is formed, wherein said analyte sensing element retains body fluid from said animal body after said analyte sensing element is removed from said animal body; and forming a refined analyte measurement based on said raw analyte measurement after said analyte sensing element is removed from said animal body.

16. The method of claim 15, wherein said analyte sensing element comprises an indicating electrode and wherein said body fluid is maintained in contact with said indicating electrode after said analyte sensing element is removed from said animal body.

17. A method, comprising:
providing an analyte sensing element adapted to be introduced into an animal body and adapted to retain body fluid from the animal body after said analyte sensing element is removed from the animal body; and coupling to said analyte sensing element a device adapted to provide electric power to said analyte sensing element, said device adapted to form a raw analyte measurement based on analyte sensed by said analyte sensing element before removal of the analyte sensing element from the animal body and adapted to form a refined analyte measurement based on said raw analyte measurement after removal of said analyte sensing element from the animal body.

* * * * *